(12) United States Patent
Ramraj et al.

(10) Patent No.: US 9,289,268 B2
(45) Date of Patent: Mar. 22, 2016

(54) TARGET LOCATION BY TRACKING OF IMAGING DEVICE

(75) Inventors: Sankaralingam Ramraj, Sunnyvale, CA (US); Sohail Sayeh, San Ramon, CA (US); Calvin R. Maurer, Jr., Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 75 days.

(21) Appl. No.: 13/271,007

(22) Filed: Oct. 11, 2011

(65) Prior Publication Data

US 2012/0265060 A1    Oct. 18, 2012

Related U.S. Application Data

(63) Continuation of application No. 12/214,885, filed on Jun. 19, 2008, now abandoned.

(60) Provisional application No. 60/936,388, filed on Jun. 19, 2007.

(51) Int. Cl.
| | | |
|---|---|---|
| A61B 5/05 | (2006.01) | |
| A61B 19/00 | (2006.01) | |
| A61B 6/04 | (2006.01) | |
| A61B 6/08 | (2006.01) | |
| A61B 8/08 | (2006.01) | |
| A61B 8/00 | (2006.01) | |
| A61N 5/10 | (2006.01) | |
| G06T 7/20 | (2006.01) | |
| A61B 6/00 | (2006.01) | |

(52) U.S. Cl.
CPC ............. *A61B 19/52* (2013.01); *A61B 6/0457* (2013.01); *A61B 6/08* (2013.01); *A61B 6/527* (2013.01); *A61B 6/5247* (2013.01); *A61B 6/541* (2013.01); *A61B 6/547* (2013.01); *A61B 8/0833* (2013.01); *A61B 8/4218* (2013.01); *A61B 8/4245* (2013.01); *A61B 8/4416* (2013.01); *A61B 8/5276* (2013.01); *A61B 19/5244* (2013.01); *A61N 5/1049* (2013.01); *G06T 7/20* (2013.01); *A61B 6/4405* (2013.01); *A61B 6/4464* (2013.01); *A61B 6/4476* (2013.01); *A61B 8/4472* (2013.01); *A61B 19/54* (2013.01); *A61B 2019/5238* (2013.01); *A61B 2019/5276* (2013.01); *A61N 5/1067* (2013.01); *A61N 2005/1051* (2013.01); *A61N 2005/1059* (2013.01); *G06T 2207/30004* (2013.01)

(58) Field of Classification Search
CPC ..................................................... G01Q 20/02
See application file for complete search history.

(56) References Cited

U.S. PATENT DOCUMENTS

| | | |
|---|---|---|
| RE30,397 E | 9/1980 | King |
| 4,583,538 A | 4/1986 | Onik et al. |
| 4,770,182 A | 9/1988 | Damadian et al. |
| 4,791,934 A | 12/1988 | Brunnett |
| 4,945,478 A | 7/1990 | Merickel et al. |

(Continued)

OTHER PUBLICATIONS

Webb (Motion effects in intensity modulated radiation therapy: a review, 2006).*

(Continued)

*Primary Examiner* — Joel F Brutus
(74) *Attorney, Agent, or Firm* — Lowenstein Sandler LLP (57) ABSTRACT

A method and apparatus for tracking a target by tracking the location of an imaging device while the imaging device is tracking the target is described.

28 Claims, 6 Drawing Sheets

(56) References Cited

U.S. PATENT DOCUMENTS

| | | | |
|---|---|---|---|
| 4,977,505 A | 12/1990 | Pelizzari et al. | |
| 5,070,401 A | 12/1991 | Salvati et al. | |
| 5,078,140 A | 1/1992 | Kwoh | |
| 5,222,499 A | 6/1993 | Allen et al. | |
| 5,230,338 A | 7/1993 | Allen et al. | |
| 5,261,404 A | 11/1993 | Mick et al. | |
| 5,299,253 A | 3/1994 | Wessels | |
| 5,313,306 A | 5/1994 | Kuban et al. | |
| 5,337,732 A | 8/1994 | Grundfest et al. | |
| 5,363,475 A | 11/1994 | Baker et al. | |
| 5,389,101 A | 2/1995 | Heilbrun et al. | |
| 5,398,684 A | 3/1995 | Hardy | |
| 5,417,210 A | 5/1995 | Funda et al. | |
| 5,419,320 A | 5/1995 | Kawaguchi et al. | |
| 5,454,371 A | 10/1995 | Fenster et al. | |
| 5,458,126 A | 10/1995 | Cline et al. | |
| 5,491,510 A | 2/1996 | Gove | |
| 5,517,016 A | 5/1996 | Lesh et al. | |
| 5,531,277 A | 7/1996 | Noonan et al. | |
| 5,531,520 A | 7/1996 | Grimson et al. | |
| 5,540,229 A | 7/1996 | Collet-Billon et al. | |
| 5,546,807 A | 8/1996 | Oxaal et al. | |
| 5,562,095 A | 10/1996 | Downey et al. | |
| 5,572,999 A | 11/1996 | Funda et al. | |
| 5,585,813 A | 12/1996 | Howard | |
| 5,604,848 A | 2/1997 | Harada et al. | |
| 5,608,849 A | 3/1997 | King, Jr. | |
| 5,611,025 A | 3/1997 | Lorensen et al. | |
| 5,622,170 A | 4/1997 | Schulz | |
| 5,671,381 A | 9/1997 | Strasnick et al. | |
| 5,682,886 A | 11/1997 | Delp et al. | |
| 5,704,897 A | 1/1998 | Truppe | |
| 5,740,802 A | 4/1998 | Nafis et al. | |
| 5,772,594 A | 6/1998 | Barrick | |
| 5,776,050 A | 7/1998 | Chen et al. | |
| 5,781,195 A | 7/1998 | Marvin | |
| 5,797,849 A | 8/1998 | Vesely et al. | |
| 5,800,352 A | 9/1998 | Ferre et al. | |
| 5,815,126 A | 9/1998 | Fan et al. | |
| 5,833,608 A | 11/1998 | Acker | |
| 5,833,627 A | 11/1998 | Shmulewitz et al. | |
| 5,836,954 A | 11/1998 | Heilbrun et al. | |
| 5,842,473 A | 12/1998 | Fenster et al. | |
| 5,855,553 A | 1/1999 | Tajima et al. | |
| 5,868,673 A | 2/1999 | Vesely | |
| 5,871,018 A | 2/1999 | Delp et al. | |
| 5,882,206 A | 3/1999 | Gillio | |
| 5,887,121 A | 3/1999 | Funda et al. | |
| 5,891,034 A | 4/1999 | Bucholz | |
| 5,892,538 A | 4/1999 | Gibas | |
| 6,016,439 A | 1/2000 | Acker | |
| 6,106,464 A | 8/2000 | Bass et al. | |
| 6,167,296 A | 12/2000 | Shahidi | |
| 6,272,366 B1 | 8/2001 | Vining | |
| 6,314,312 B1 | 11/2001 | Wessels et al. | |
| 6,359,190 B1 | 3/2002 | Ter-Ovanesyan et al. | |
| 6,895,268 B1 | 5/2005 | Rahn et al. | |
| 6,932,089 B1* | 8/2005 | Cinquin et al. | 128/897 |
| 7,623,623 B2 | 11/2009 | Raanes et al. | |
| 7,798,970 B2 | 9/2010 | Lo et al. | |
| 2002/0049375 A1 | 4/2002 | Strommer et al. | |
| 2002/0115931 A1 | 8/2002 | Strauss et al. | |
| 2003/0073901 A1 | 4/2003 | Simon et al. | |
| 2003/0084906 A1 | 5/2003 | Roe | |
| 2003/0130576 A1 | 7/2003 | Seeley et al. | |
| 2004/0097806 A1 | 5/2004 | Hunter et al. | |
| 2004/0171924 A1 | 9/2004 | Mire et al. | |
| 2005/0054895 A1 | 3/2005 | Hoeg et al. | |
| 2005/0085717 A1 | 4/2005 | Shahidi | |
| 2005/0085718 A1 | 4/2005 | Shahidi | |
| 2005/0182316 A1* | 8/2005 | Burdette et al. | 600/424 |
| 2005/0215888 A1 | 9/2005 | Grimm et al. | |
| 2005/0228255 A1 | 10/2005 | Saracen et al. | |
| 2006/0004281 A1 | 1/2006 | Saracen | |
| 2006/0020210 A1* | 1/2006 | Mendlein et al. | 600/459 |
| 2006/0036162 A1 | 2/2006 | Shahidi | |
| 2006/0052694 A1 | 3/2006 | Phillips | |
| 2006/0106311 A1 | 5/2006 | Lo et al. | |
| 2006/0149418 A1* | 7/2006 | Anvari | 700/245 |
| 2006/0173291 A1 | 8/2006 | Glossop | |
| 2006/0285641 A1* | 12/2006 | Scherch | 378/65 |
| 2007/0015991 A1* | 1/2007 | Fu et al. | 600/407 |
| 2007/0038065 A1 | 2/2007 | Creighton et al. | |
| 2007/0106147 A1* | 5/2007 | Altmann et al. | 600/407 |
| 2007/0211927 A1 | 9/2007 | Groszmann et al. | |
| 2007/0276243 A1* | 11/2007 | Gerard et al. | 600/440 |
| 2008/0049896 A1* | 2/2008 | Kuduvalli | 378/65 |
| 2009/0003523 A1 | 1/2009 | Raanes et al. | |
| 2009/0069794 A1* | 3/2009 | Kurtz | 606/4 |

OTHER PUBLICATIONS

"Calypso® 4D Localization System™ ¿ ½ Technology Overview", downloaded from htttp://www.calypsomedical.com/HealthCareTechnology.aspx, 2007, 2 pages.

P. Parikh et al., "Dosimetric effects of a 4D Magnetic Localization System for LINAC Beam Gating on Prostate and Lung Radiation Therapy", Jul. 26, 2007, 1 page.

D.M. Shepard et al., "Latency Measurements and Demonstration of a 4D Electromagnetic Localization System for LINAC Beam Gating", Jul. 25, 2007, 1 page.

E Coste-Maniere et al., Robotic whole body stereotactic radiosurgery: clinical advantages of the CyberKnife® integrated system, Int J Medical Robotics and Computer Assisted Surgery 2005; pp. 28-39.

Jay B West et al., "Designing Optically Tracked Instruments for Image-Guided Surgery", IEEE Transactions on Medical Imaging, vol. 23, No. 5, May 2004, pp. 533-545.

Calypso Abstract, D.M. Shepard et al., "Latency Measurements and Demonstration of a 4D Magnetic Localization System for LINAC beam gating", AAPM 2007 conference, 1 page.

Calypso Abstract, Latency Measurements and Demonstration of a 4D Magnetic Localization System for LINAC beam gating, AAPM 2007 conference, 2 pages.

Calypso Abstract, Dosimetric effects of a 4D Magnetic Localization System for LINAC beam gating on prostate and lung radiation therapy, AAPM 2007 conference, 2 pages.

Calypso Abstract, Calypso® Medical 4D Localization System, AAPM 2007 conference, 1 page.

International Search Report and Written Opinion of the International Searching Authority mailed Sep. 23, 2008, for PCT Patent Application No. PCT/US2008/07717, filed Jun. 19, 2008.

International Preliminary Report mailed Jan. 7, 2010, for PCT Patent Application No. PCT/US2008/07717, filed Jun. 19, 2008, 7 pages.

* cited by examiner

TARGET LOCATION BY TRACKING OF IMAGING DEVICE

CROSS-REFERENCE TO RELATED APPLICATIONS

This application is a continuation of U.S. patent application Ser. No. 12/214,885, filed Jun. 19, 2008, which claims the benefit of U.S. Provisional Patent Application No. 60/936, 388, filed Jun. 19, 2007, both of which are hereby incorporated by reference herein.

TECHNICAL FIELD

Embodiments of the present invention relate to the field of radiation treatment, and in particular, to a system of tracking the movement of a pathological anatomy during respiration.

BACKGROUND

One challenge facing the delivery of radiation to treat pathological anatomies such as tumors or lesions is identifying the location of the target (i.e. tumor location within a patient). The most common technique currently used to identify and target a tumor location for treatment involves a diagnostic X-ray or fluoroscopy system to image the patient's body to detect the position of the tumor. This technique assumes that the tumor is stationary. Even if a patient is kept motionless, radiation treatment requires additional methods to account for movement due to respiration, in particular when treating a tumor located near the lungs. Breath hold and respiratory gating are two conventional methods used to compensate for target movement during respiration while a patient is receiving conventional radiation treatments.

Breath hold requires the patient to hold his or her breath at the same point in the breathing cycle and only treats the tumor when the tumor is stationary. A respirometer is often used to measure the tidal volume and ensure the breath is being held at the same location in the breathing cycle during each irradiation. Such a breath hold method takes longer than a standard treatment and often requires training the patient to hold his or her breath in a repeatable manner.

Respiratory gating is the process of turning on the radiation beam as a function of a patient's breathing cycle. When using a respiratory gating technique, treatment is synchronized to the individual's breathing pattern, limiting the radiation beam delivery to only one specific part of the breathing cycle and targeting the tumor only when it is in the optimum range. Such a respiratory gating method requires the patient to have many sessions of training and many days of practice to breathe in the same manner for long periods of time. A system implementing the respiratory gating method may also require healthy tissue to be irradiated before and after the tumor passes into view to ensure complete coverage of the tumor.

Attempts have been made to avoid the burdens placed on a patient from breath hold and respiratory gating techniques. Some methods for tracking the movement of a tumor or other target use imaging devices to capture the internal structure of a patient's body. One imaging modality that is commonly used in medical applications is ultrasound. Ultrasound systems create images of internal structure by detecting reflection signatures resulting from the propagation of high-frequency sound waves into the internal structure.

Conventional ultrasound systems are not suitable for use in target tracking applications because the imaging field of such systems is typically small, so that tissue movement affecting the imaged area is more likely to move a target out of the imaging field. Furthermore, repositioning of the ultrasound transducer to maintain image quality may require intervention by an operator whose presence in a treatment room may be disruptive, particularly during a treatment session.

BRIEF DESCRIPTION OF THE DRAWINGS

The present invention is illustrated by way of example, and not by way of limitation, in the figures of the accompanying drawings.

DETAILED DESCRIPTION

Described herein is a method and apparatus for tracking the movement of a target such as a pathological anatomy. The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

According to one embodiment of the invention, a target location may be tracked relative to a global reference point by determining a positional offset between the target location and an imaging device, then determining a positional offset between the imaging device and the global reference point. The positional offsets may then be added to determine a global offset between the target and the global reference point.

The imaging device may be any device capable of locating a target, such as a tumor, within a patient's body. For example, the imaging device may capture images of the target using modalities such as X-ray or computed tomography (CT). Generally, imaging refers to the techniques and processes used to create images of an object. Medical imaging is concerned primarily with the creation of images of structures within the human body. An imaging device is an apparatus used for creating images. The images can be two-dimensional (2D) or three-dimensional (3D). If the images are digital, the elements of 2D and 3D images are often referred to as pixels (picture elements) and voxels (volume elements), respectively. The images generally represent a property of the object and in the case of medical images a property of living tissue or agents administered to living tissue such as intravenous, catheter, and orally administered dyes, contrast agents and radiopharmaceuticals. The properties of living tissue are generally inferred from an observed signal. Examples of signals include the measurement of the transmission of x-rays through the body (the basis for projection radiography and x-ray computed tomography), the measurement of the reflection of ultrasound waves transmitted through the body (the basis for ultrasonography), and the measurement of gamma rays emitted by radiopharmaceuticals which have been selectively deposited in the body (the basis for nuclear medicine imaging and positron emission tomography).

In one embodiment, the imaging device may be an ultrasound scanner, and the location of the tumor may be determined as a positional offset between the tumor and the ultrasound scanner. The ultrasound scanner may then be tracked by a tracking device such as an X-ray imager, which determines the positional offset between the ultrasound scanner and the X-ray imager. If the offset between the X-ray imager and the global reference point is known, then the offset between the X-ray imager and the global reference point, the offset between the X-ray imager and the ultrasound scanner, and the offset between the ultrasound scanner and the target may all be added to determine the offset between the target and the global reference point.

In a radiation treatment application, the tracked location of the target may be used to direct a linear accelerator (LINAC) and/or the treatment couch so that the beam of the LINAC intersects the target, which may identify a location in a pathological anatomy. In one embodiment, the target may be tracked periodically. The LINAC is mounted on a robotic arm that receives the periodically updated location of the target and adjusts the orientation of the LINAC accordingly. Furthermore, the treatment couch may also receive the periodically updated location of the target and adjusted. In this way, the intersection of the LINAC beam with the target may be maintained for a desired duration of a treatment session despite movement of the target caused by factors such as respiration, heartbeat, or other causes of movement.

In other embodiments of the invention, the tracking device may be an optical system, such as a camera, or any other device that can determine positional information. In one embodiment, the tracking device may be an optical system that tracks the position of the imaging device by detecting the position of light-emitting diodes (LEDs) situated on the imaging device. Such an optical system may include infrared cameras for detecting the position of the LEDs, which may emit light in the infrared spectrum. In an alternative embodiment, if the imaging device, such as an ultrasound scanner, is mounted on a robotic arm, then the tracking device may be implemented using sensors or mechanical encoders on the robot arm that can determine the position of the imaging device based on the joint orientations of the robot arm, as discussed below in relation to FIG. 3.

Figure 1:
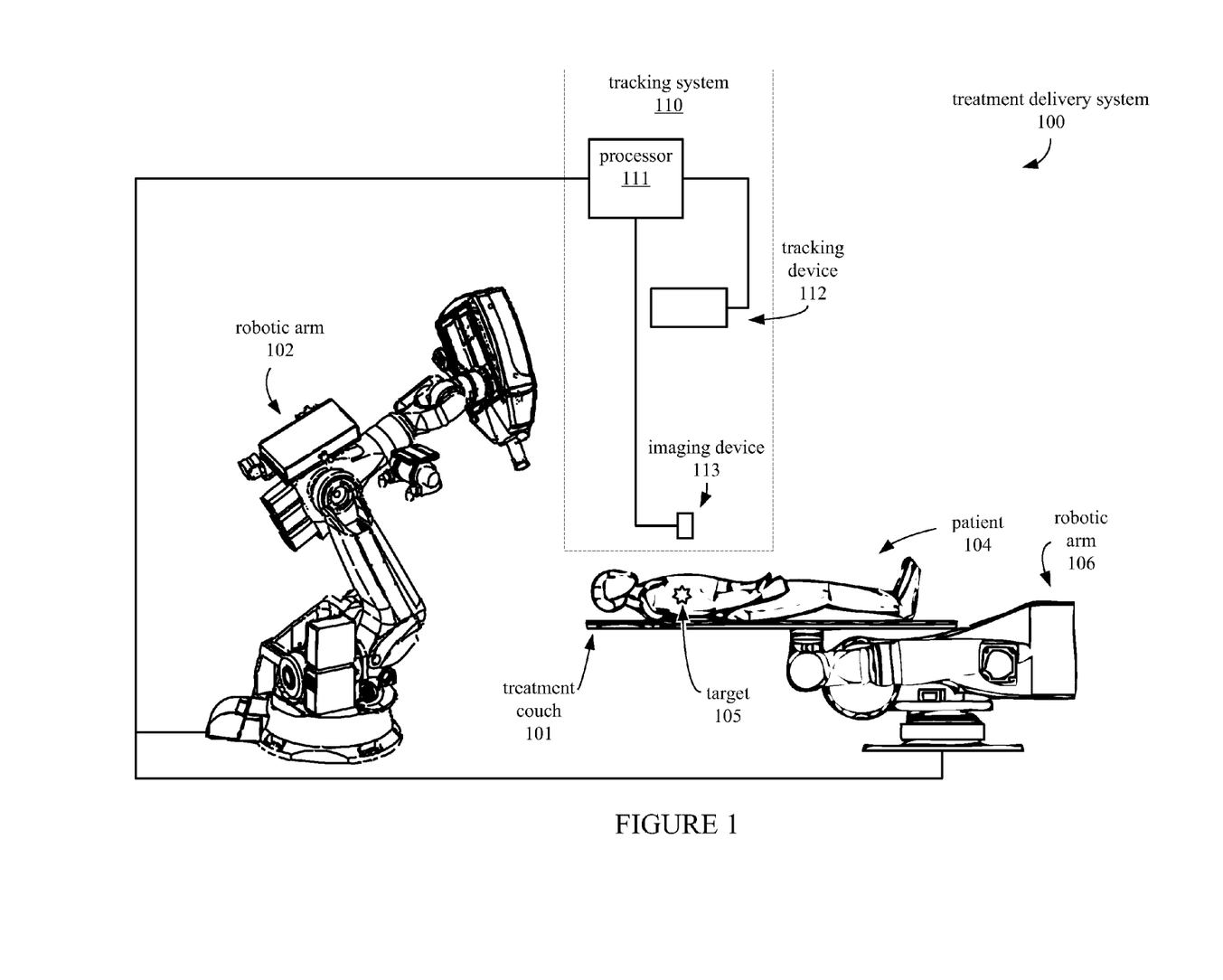
FIG. 1 illustrates a system for tracking motion of a target within the body of a patient and delivering treatment to the tracked target, according to one embodiment of the invention.

FIG. 1 illustrates a treatment delivery system 100 for delivering radiation therapy to a target area within a patient according to one embodiment of the invention. Treatment delivery system 100 includes tracking system 110, treatment couch 101, robotic arm 102, and linear accelerator (LINAC) 103, which is mounted on robotic arm 102. Tracking system 110 further includes a processor 111, a tracking device 112, and an imaging device 113. Treatment couch 101 may be designed to support a patient 104. A target 105 within the patient 104 may be the site of a pathological anatomy to receive radiation treatment.

The purpose of a radiation treatment session may be to deliver radiation to target 105 by intersecting target 105 with a radiation beam produced by LINAC 103. Target 105 may be moving, for example, as a result of respiration or heartbeat of the patient 104. Thus, tracking system 110 may be used to track the location of target 105 as it moves so that the intersection of target 105 with the beam of LINAC 103 may be maintained. Tracking system 110 may send positional information identifying the location of target 105 to robotic arm 102 so that robotic arm 102 can adjust the position of LINAC 103 to maintain the intersection of the LINAC beam with target 105. In one embodiment, tracking system 110 may send the location of target 105 continuously to robotic arm 102. Alternatively, the location information may be sent periodically or may be sent only when the location of target 105 changes. In another embodiment, the tracking system 110 may send the positional information identifying the location of target 105 to robotic arm 106 of the treatment couch 101 so that robotic arm 106 can adjust the position of the treatment couch 101 to move the target 105 to maintained the intersection with the LINAC beam. Alternatively, both robotic arms 106 and 102 may be utilized in conjunction to maintain the intersection of the LINAC beam and target.

Tracking system 110 includes processor 111, which may be connected to tracking device 112 and imaging device 113. Imaging device 113 may be used to track the location of target 105 relative to imaging device 113. For example, an image captured by imaging device 113 may indicate a positional offset between target 105 and imaging device 113 or another reference point, such as a fiducial marker. Imaging device 113 may be mobile, and may be repositioned for such reasons as maintaining image quality, for registration purposes, or to keep target 105 within an imaging field of imaging device 113. Tracking device 112 may then track the location of imaging device 113. For example, tracking device 112 may determine a positional offset between imaging device 113 and tracking device 112 or some other reference point. Information about the location of target 105 and imaging device 113 can then be sent to processor 111, where a global position of the target 105 may be calculated. For example, a global reference point located in the treatment room may be used for identifying the locations of objects within the treatment room. Accordingly, processor 111 may determine the location of the target 105 relative to the global reference point using positional data collected by tracking device 112 and imaging device 113.

Figure 2:
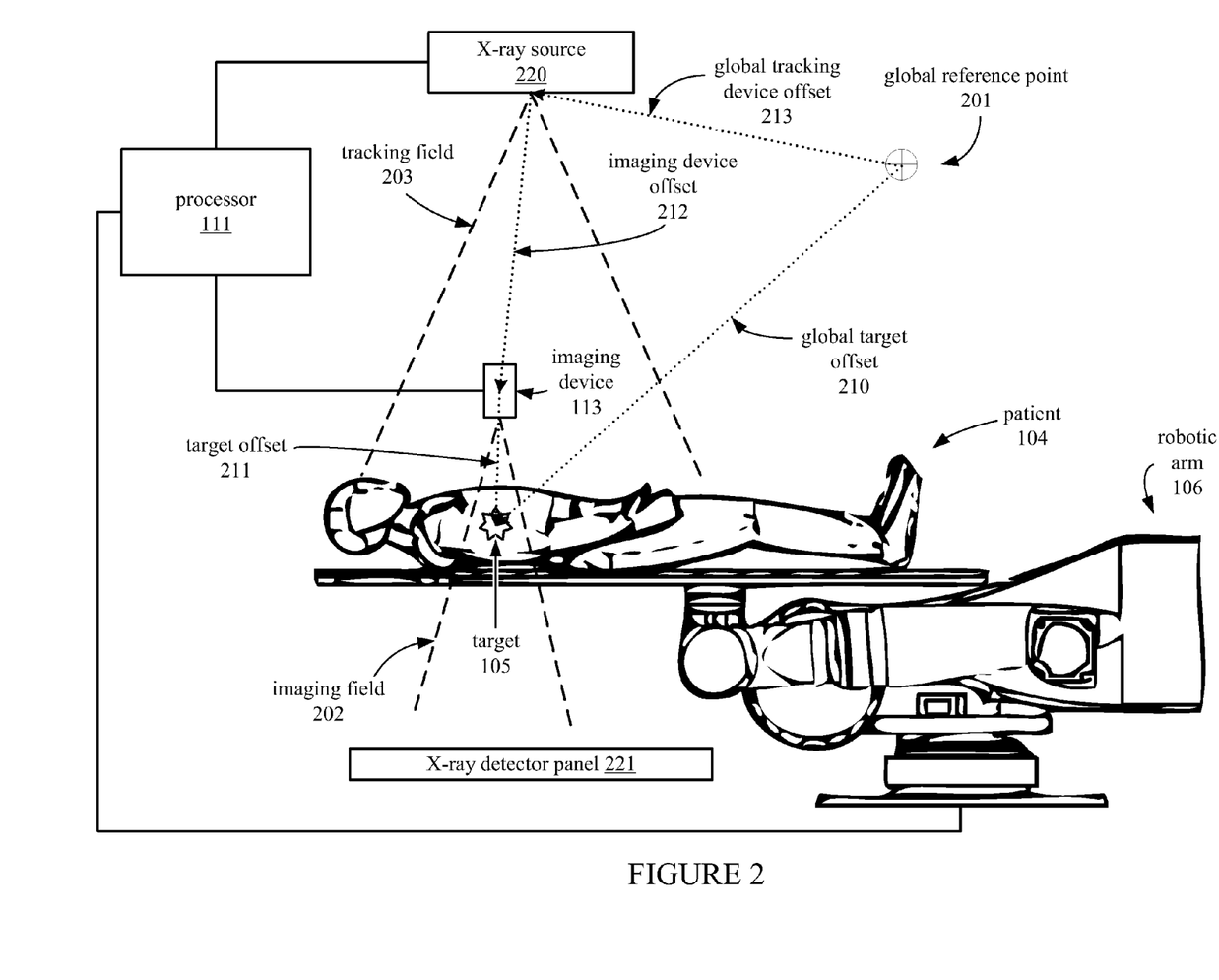
FIG. 2 illustrates components of a target tracking system, according to one embodiment of the invention.

FIG. 2 illustrates components of tracking system 110 in greater detail, according to one embodiment where tracking device 112 is an X-ray imaging system. In tracking system 110, X-ray source 220 and X-ray detector 221 are components of the X-ray imaging system operating as tracking device 112. It should be noted that although only one X-ray detector panel 221 is illustrated in FIG. 2, alternative embodiments may include additional detector panels. X-ray source 220 has a tracking field 203, where objects located within tracking field 203 may be effectively tracked. Similarly, imaging device 113 has an imaging field 202, where objects within imaging field 202 may be effectively captured in an image by imaging device 113. Global reference point 201 is a location that can be used for designating other locations, particularly in terms of a positional offset between the global reference point 201 and the location being designated. A positional offset simply describes the location of one reference point relative to another reference point. For example, a positional offset in three-dimensional space may be represented as a vector having x, y, and z components in a Cartesian coordinate system. The target offset 211 is the positional offset between the imaging device 113 and the target 105. The imaging device offset 212 is the positional offset between the X-ray source 220 and the imaging device 113. The global tracking device offset 213 is the positional offset between the global reference point 201 and the X-ray source 220. The global target offset is the positional offset between the global reference point 201 and the target 105.

In one embodiment, the global reference point 201 may be the tracking (e.g., imaging) center of tracking device 112, which includes X-ray source 220 and X-ray detector panel 221. Such a tracking center may coincide with a treatment isocenter, but not necessarily so. It should be noted that global reference point 201 has been positioned away from the other figure elements for ease of illustration.

Imaging device 113 may in one embodiment be an ultrasound scanner. Alternatively, imaging device 113 may be some other type of device that is capable of locating a target, such as an X-ray imager or an electromagnetic coil array. Imaging device 113 may be positioned so that the imaging field 202 of imaging device 113 encompasses target 105. For example, if an ultrasound scanner is used as imaging device 113, the transducer of the ultrasound scanner may be placed against the skin of patient 104 near target 105. Alternatively, if another imaging modality such as X-ray imaging is used, imaging device 113 may be placed farther away from the patient 104, as long as the position of target 105 may still be captured by imaging device 113.

Imaging device 113 may operate by capturing an image of target 105. The image can then be used to determine the location of target 105 relative to imaging device 113, which is the target offset 211. For example, the size, position, and orientation of target 105 as captured in an image by imaging device 113 may indicate the position and orientation of target 105 in real space, relative to imaging device 113. The position of target 105 may also be determined by reference to surrounding structures having known locations captured in an image along with target 105.

X-ray source 220 may be positioned so that tracking field 203 of X-ray source 220 encompasses imaging device 113. In one embodiment, X-ray source 220 is mounted in a fixed position. For example, X-ray source 220 may be mounted on a wall or ceiling of a treatment room where a radiation treatment session is taking place. Alternatively, X-ray source 220 may be mobile, so that X-ray source 220 can be repositioned to maintain imaging device 113 within tracking field 203.

X-ray source 220 and X-ray detector panel 221 determine the imaging device offset 213, which is the location of imaging device 113 relative to X-ray source 220. For example, the X-ray source 220 and X-ray detector panel 221 may capture an image of imaging device 113. The size, orientation, and position of imaging device 113 as represented within the captured image may indicate the position of imaging device 113 relative to X-ray source 220 in real space. The position of imaging device 113 may also be determined by reference to other structures having known locations captured in an image along with imaging device 113.

The global position of the target 105 may be determined by processor 111. Specifically, processor 111 may determine the position of the target 105 relative to global reference point 201. Processor 111 may base this calculation on images captured by X-ray source 220 and X-ray detector panel 221, and also from imaging device 113. The image data received by processor 111 in one embodiment may be, for example, raw or processed image data. Alternatively, the positional offsets of the target 105 and the imaging device 113 may be transmitted to the processor, if the positional offsets have already been determined from the raw data.

The processor 111 can determine the global target offset 210 by adding the positional offsets, including the target offset 211, the imaging device offset 212, and the global tracking device offset 213. Imaging device 113 may capture an image of target 105 that may be used to determine the target offset 211. Tracking device 112 may then capture an image or otherwise collect data that can be used to determine the imaging device offset 212. The global tracking device offset 213 may be determined as part of a calibration measurement and may be measured from part of tracking device 112 such as X-ray source 220. For example, if X-ray source 220 is mounted in a fixed location, such as on a wall or ceiling of the treatment room, the global tracking device offset 213 may be measured during or after the installation of X-ray source 220. The global tracking device offset 213 may also be determined using other imaging or tracking devices. For example, if the X-ray source 220 is movable on a track or rail, sensors on the track or rail may be used to indicate the position of the X-ray source 220. Once the target offset 211, imaging device offset 212, and global tracking device offset 213 are known, they can be added to determine the global target offset 210. This calculation may be performed by processor 111. The global target offset can then be used, for example, to control robotic arm 102 so that a beam of LINAC 103 intersects target 105. In one embodiment, the determination of global target offset 210 may be repeated so that the global location of target 105 can be continuously or periodically updated. Alternatively, the determination of the global target offset 210 may be performed in response to detecting or anticipating movement by target 105.

In other embodiments, a detector panel such as X-ray detector panel 221 may not be required. For example, a camera or other optical system in conjunction with light-emitting diodes (LEDs) attached to imaging device 113 may be used as tracking device 112. The camera may track imaging device 113 by capturing images including the LEDs, without the need for detector panel 221. Aside from X-ray imagers, cameras, or similar imaging systems, other types of tracking devices can also be used to perform the functions of tracking device 112.

Figure 3:
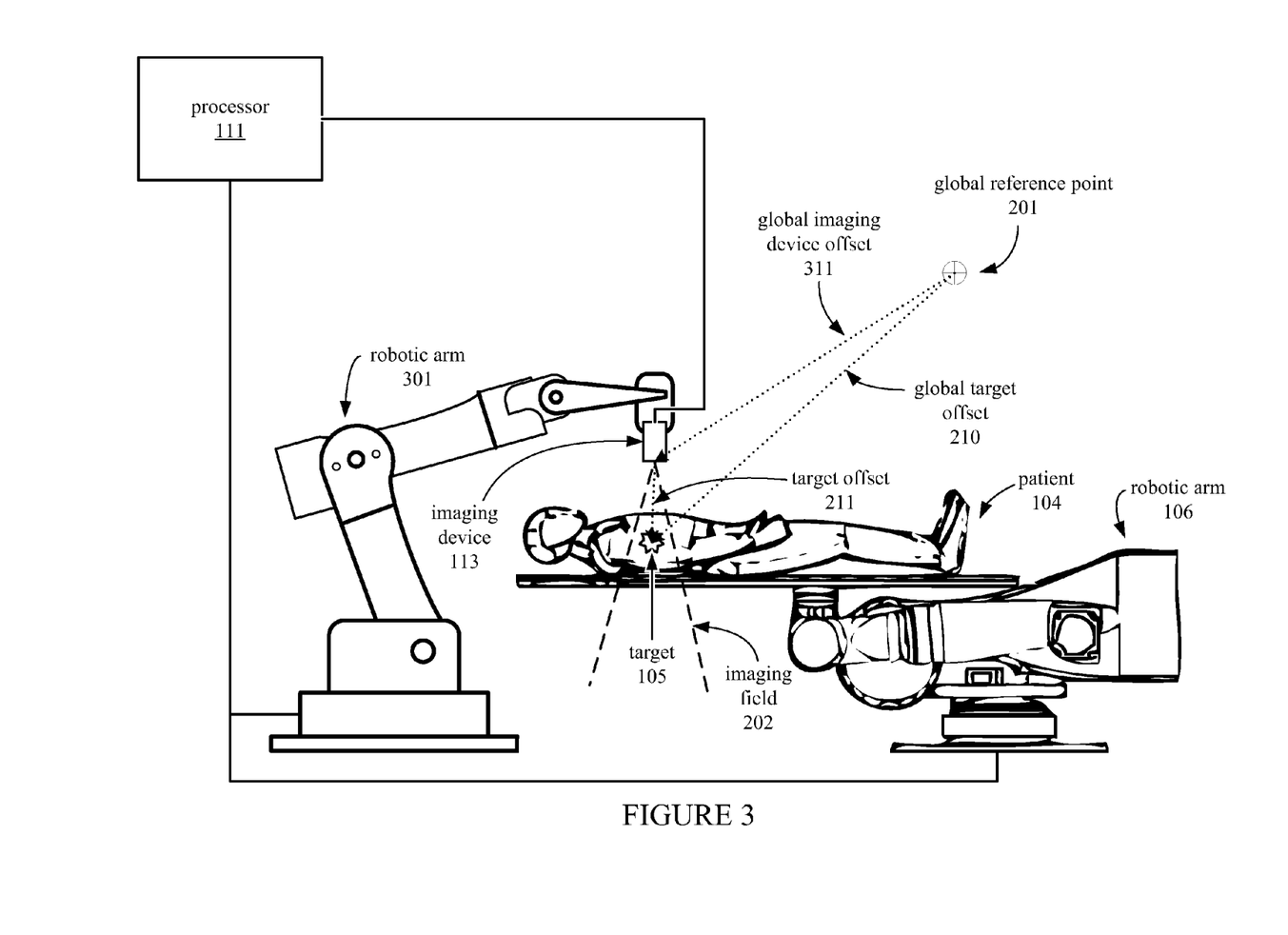
FIG. 3 illustrates a target tracking system utilizing an imaging device attached to a robotic arm, according to one embodiment of the invention.

FIG. 3 illustrates a tracking system for tracking a target 105 within patient 104 using a robotic arm system according to one embodiment of the invention. The tracking system includes a processor 111, an imaging device 113, and a robotic arm 301 and determines a global target offset 210 by summing a global imaging device offset 311 and a target offset 211. Imaging device 113 has an imaging field 202. Objects within the imaging field 202 may be effectively captured in an image by imaging device 113. Offsets 210, 211, and 311 may be described by vectors in three-dimensional space.

Imaging device 113 is mounted on robotic arm 301 so that robotic arm 301 can control the movement, orientation, and position of imaging device 113. Depending on the type of imaging device 113 being used, robotic arm 301 may hold the imaging device 113 at a distance from the target 105 or may contact a skin surface of patient 104 with imaging device 113. For example, if imaging device 113 is an ultrasound scanner, robotic arm 301 may position the ultrasound scanner so that its transducer contacts the skin surface of patient 104. Robotic arm 301 may also be used to reposition imaging device 113 so that target 105 remains within the imaging field 202 of imaging device 113. An ultrasound scanner used as imaging device 113, for instance, may have a small imaging field 202 such that movement of the patient 104 due to respiration or heartbeat may tend to move target 105 outside imaging field 202. Thus, robotic arm 301 may be used to compensate for the movement of target 105. In one embodiment, processor 111 may also be used to monitor the images captured by imaging device 113, detect when target 105 is not within imaging field 202, and direct robotic arm 301 to move imaging device 113. Alternatively, the imaging device may be moved according to a defined path. For example, if the movement of target 105 can be described as a periodic pattern, the imaging device may be moved according to that pattern. The imaging device may also be moved for registration purposes. For example, the imaging device may be moved to a known location in a treatment room so that images captured by the imaging device may be correlated with the known location for calibration purposes.

As previously described, imaging device 113 may be used to determine target offset 211, which is the position of target 105 relative to imaging device 113. Global imaging device offset 311 may then be determined using sensors or other mechanical encoders on robotic arm 301. For example, sensors mounted on the joints of robotic arm 301 may indicate the orientation of each joint. The joint orientations can then be used to calculate the position of the imaging device 113 relative to global reference point 201. Once the target offset 211 and the global imaging device offset 311 are known, the global target offset 210 may be calculated by summing the target offset 211 and the global imaging device offset 311. This calculation may be performed by processor 111. In one embodiment, processor 111 may receive offsets 211 and 311 from robotic arm 301 and imaging device 113. Alternatively, processor 111 may calculate offsets 211 and 311 from raw data received from robotic arm 301 and imaging device 113. Aside from mechanisms such as robotic arm 301, imaging device 113 may also be positioned using other types of positioning mechanisms.

Figure 4:
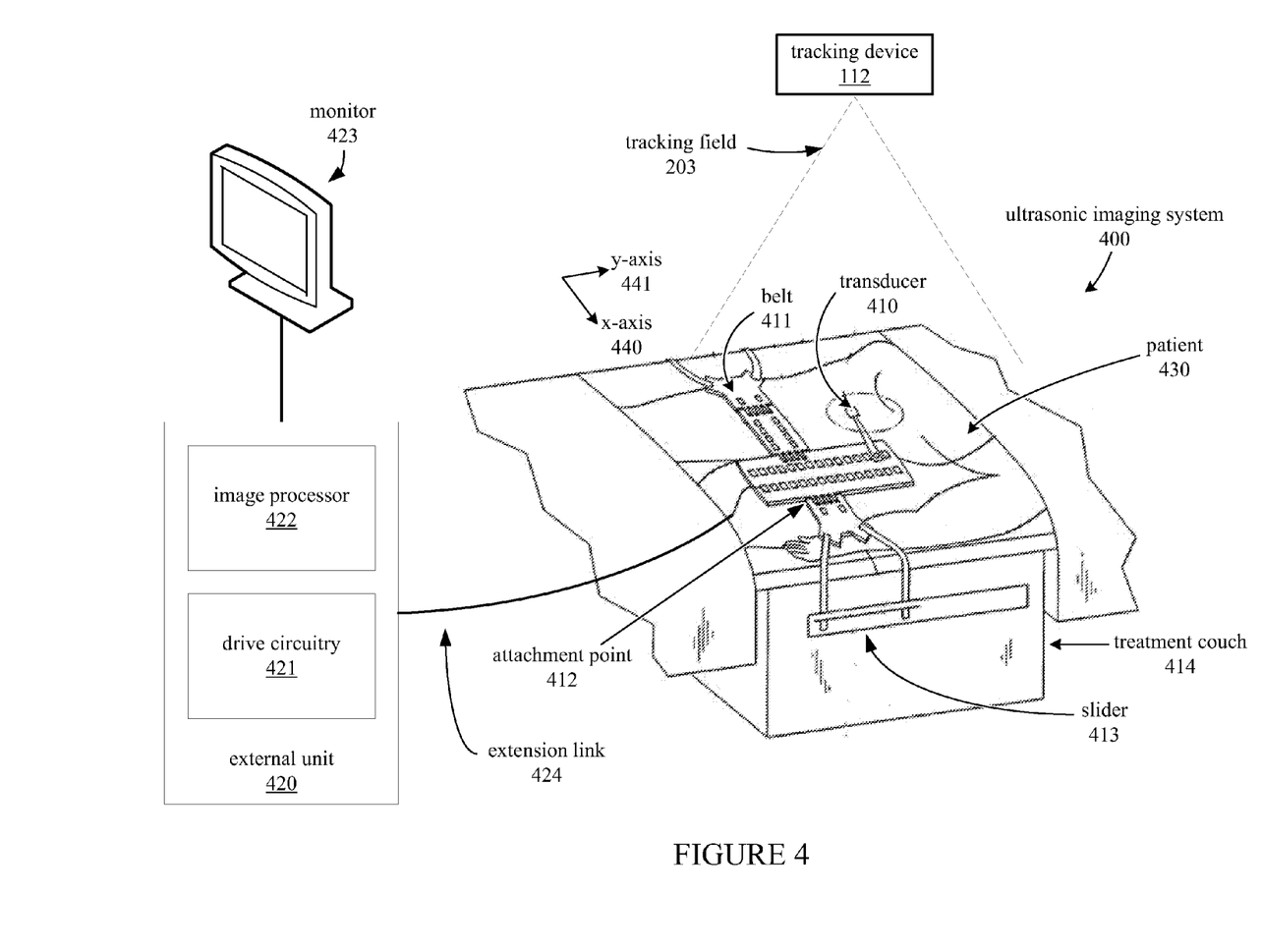
FIG. 4 illustrates an ultrasonic imaging system that can be used as an imaging device, according to one embodiment of the invention.

FIG. 4 illustrates an ultrasonic imaging system that can be positioned using a belt mechanism, according to one embodiment of the invention. Ultrasonic imaging system 400 may be used as imaging device 113, and includes an ultrasonic transducer 410 attached to belt 411 at attachment point 412. Belt 411 is then attached to treatment couch 414 by slider 413. The transducer 410 is connected through extension link 424 to external unit 420, which includes image processor 422 and drive circuitry 421. External unit 420 is further connected to a monitor 423. Tracking device 112 may be positioned so that tracking field 203 encompasses transducer 410, so that tracking device 112 can be used to track the position of transducer 410.

While patient 430 is lying on treatment couch 414, transducer 410 is held in place on the skin surface of patient 430 using belt 411. Transducer 410 is attached to belt 411 at attachment point 412, which in one embodiment, can be removed from and reattached to belt 411 so that the position of transducer 410 can be adjusted along the x-axis 440. Alternatively, attachment point 412 may be a sliding attachment that allows repositioning of transducer 410 without removal and reattachment. Belt 411 may also be attached to treatment couch 414 at slider 413. Slider 413 may allow the belt 411 to be repositioned along the length of treatment couch 414, along the y-axis 441. Alternatively, other types of repositioning mechanisms may be used other than a slider. For example, belt 411 may be repositioned by detaching belt 411 and reattaching belt 411 at a different location. In other embodiments, belt 411 may not be attached to treatment couch 414.

The belt assembly, including belt 411 attachment point 412, and slider 413, keeps transducer 410 in contact with the skin surface of patient 430 at a particular location. Transducer 410 may then be used as imaging device 113. The location of a target 105 with respect to transducer 410 may be determined using an image of the target 105 captured by the ultrasonic imaging system 400. The location of transducer 410 with respect to tracking device 112 may be determined using tracking device 112. The global position of the target 105 with respect to the global reference point 201 can then be determined by adding the appropriate offsets, as previously described.

Drive circuitry 421 and image processor 422 may be kept apart from transducer 410 so that transducer 410 can be more easily repositioned. Thus, drive circuitry 421 and image processor 422 may be kept in an external unit 420, which may be a box or other enclosure. Drive circuitry 421 may be connected to transducer 410 through extension link 424 so that drive circuitry 421 can provide the signals to the transducer 410 required to conduct the ultrasound imaging. Image processor 422 can also be connected to transducer 410 through extension link 424 so that image processor 422 can convert the signals received from the transducer 410 into an image to be displayed on monitor 423. Extension link 424 may be any medium through which signals can be transmitted, such as a cable or a wireless link, while allowing transducer 410 to be moved independently from external unit 420.

The ultrasonic imaging system 400 may adjust parameters such as gain, transducer pressure, transmit frequency, receive frequency, and dynamic range in response to input received from other devices. For example, ultrasonic imaging system 400 may adjust its transmit frequency based on an input received from processor 111 requesting such an adjustment. In addition, belt 411 of ultrasonic imaging system 400 may include a gel container that is configured to apply gel between the skin surface of the patient 430 and the transducer 410. In one embodiment, application of the gel can be initiated by a request sent from another device. For example, processor 111 may determine that a reapplication of gel would improve the quality of images produced by ultrasonic imaging system 400. Processor 111 can send an input to ultrasonic imaging system 400 to initiate the application of gel.

Figure 5:
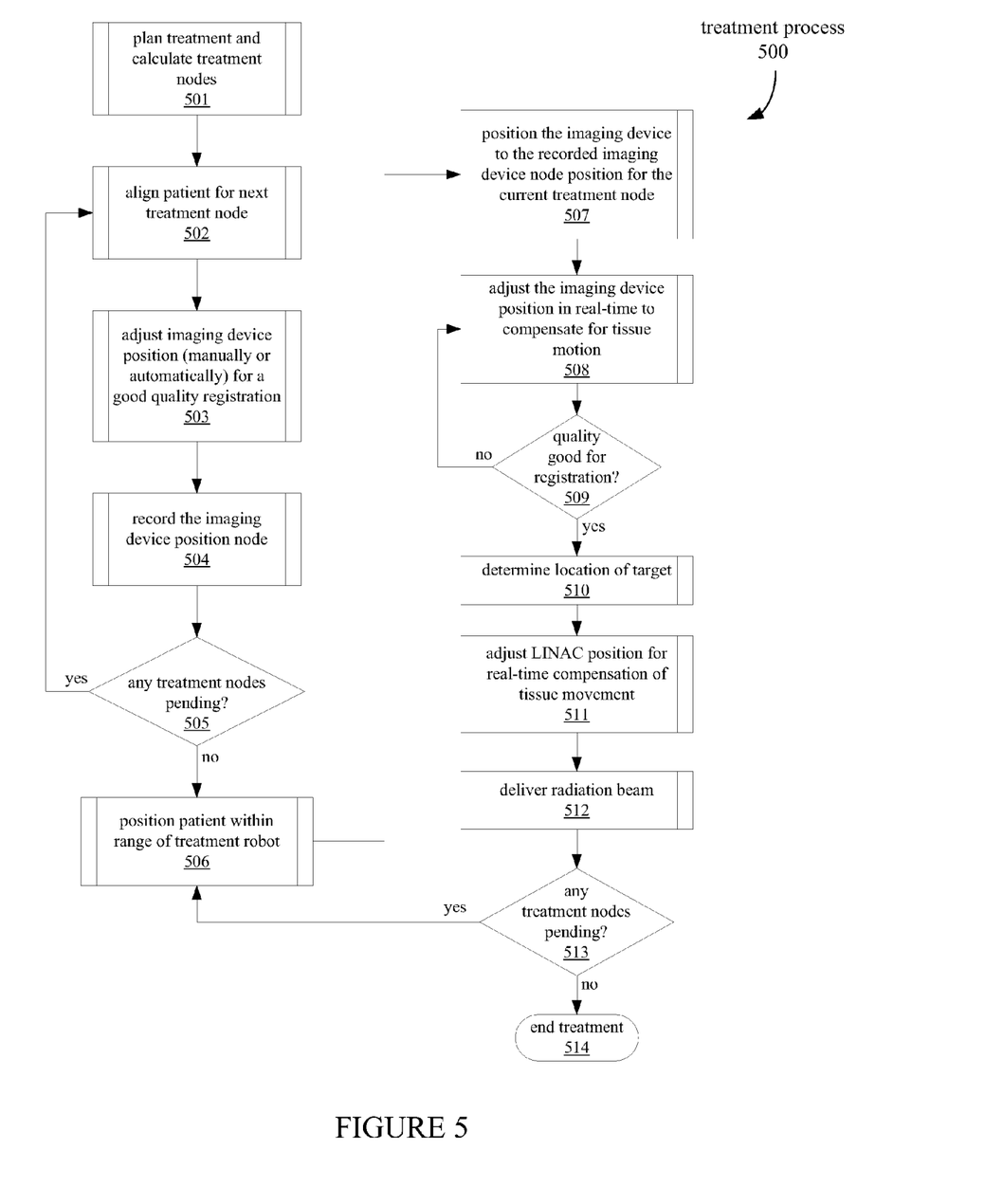
FIG. 5 is a flow diagram illustrating a process for administering radiation treatment while tracking the treatment target according to one embodiment of the invention.

FIG. 5 is a flow diagram illustrating a process for administering radiation treatment while tracking the treatment target according to one embodiment of the invention. At block 501 of treatment process 500, the treatment is planned and treatment nodes are calculated. The treatment planning may include determining such details as the radiation dosage needed to complete the treatment or the angles at which the radiation beam will intersect the target 105. The process may also determine a number of treatment nodes, which represent spatial locations from which the LINAC 103 delivers a radiation beam to the target 105.

At block 502, the patient 104 is aligned for a treatment node. The patient 104 may be placed on a treatment couch 101 so that the target 105 within patient 104 is positioned to receive a radiation beam delivered from the treatment node.

With the patient 104 appropriately aligned, the position of an imaging device 113 is adjusted in block 503 so that an image produced by the imaging device 113 is of sufficient quality to be used for registration with corresponding images, such as CT or X-ray images. For example, an ultrasound scanner used as imaging device 113 may be adjusted to maintain the target 105 within an imaging field of the scanner, or may be adjusted to maintain an optimal angle for imaging the target 105. The adjustment of the position of imaging device 113 can be done manually or by an automatic mechanism. For example, the imaging device 113 may be automatically repositioned based on the location or orientation of the target 105 within an image captured by imaging device 113.

Once the position of the imaging device 113 has been adjusted, the location of the imaging device 113 is recorded as a node for the corresponding treatment node designating the position of LINAC 103, according to block 504. In an alternative embodiment, other parameters may also be recorded with the imaging device node. For example, if the imaging device 113 is an ultrasound scanner, parameters such as gain, transducer pressure, transmit frequency, receive frequency, and dynamic range may be recorded. The recorded imaging device node parameters may be stored in any of a number of storage locations. For example, the node parameters may be stored in the imaging device itself, in another component of the treatment delivery system 100, or in a network location such as a Digital Imaging and Communications in Medicine (DICOM) workstation.

In block 505, if additional treatment nodes are pending, execution proceeds back to block 502. Otherwise, if imaging device nodes have been determined corresponding to each of the treatment nodes, then execution proceeds to block 506.

At block 506, patient 104 is placed within range of the treatment robot, which includes robotic arm 102 and LINAC 103. For example, patient 104 may be placed on treatment couch 101 near enough to LINAC 103 so that a beam of LINAC 103 can intersect target 105.

With the patient 104 in position to receive treatment from LINAC 103, the treatment session can begin. In block 507, the imaging device 113 is positioned at a recorded imaging device node corresponding to the initial treatment node. The recorded imaging device node may also specify parameters to be used by the imaging device 113, such as gain adjustment, transmit and receive frequency, and dynamic range. The imaging node location and other parameters are read, and then applied to the imaging device. In one embodiment, where the imaging device 113 is an ultrasound scanner having a transducer 410 attached to belt 411, the transducer 410 may be moved to the location of the imaging device node by a positioning mechanism attached to the belt 411. Alternatively, if the imaging device 113 is attached to a robotic arm 301, then the imaging device 113 may be moved to the imaging device node by the robotic arm 301. The parameters specified in the imaging device node may be sent to imaging device 113 so that imaging device 113 may adjust its parameters accordingly. In some embodiments, imaging device 113 may also automatically adjust its parameters in real-time to facilitate real-time tracking of target 105.

In block 508, the position of the imaging device 113 is adjusted to compensate for movement of target 105 caused by respiration, heartbeat, or other tissue motion of the patient 104. As in block 507, the imaging device may be adjusted using a robotic arm or other positioning mechanism. The imaging device 113 is repositioned so that the imaging device 113 can capture images of the target 105 suitable for registration with other corresponding images of the target 105, such as CT or X-ray images. The position of imaging device 113 is adjusted until the quality of the images captured by imaging device 113 is acceptable for registration, according to block 509.

If the quality of the captured images is acceptable for registration purposes, then execution proceeds from block 509 to block 510, where the location of the target 105 is determined. The location of target 105 may be determined by using an image captured by imaging device 113 to locate the target 105 relative to the imaging device 113. In one embodiment, the location of target 105 is tracked relative to imaging device 113 by detecting the edges of the structures in images captured by imaging device 113, identifying edges to be tracked, and tracking the position of the identified edge as it moves. For example, an ultrasound scanner used as imaging device 113 may determine the location of target 105 by tracking the edges of target 105 as they appear in images captured by the ultrasound scanner over time. The tracking device 112 can then be used to locate the imaging device 113 relative to a global reference point 201. The location of the target 105 relative to the global reference point can then be determined from the location of target 105 relative to the imaging device 113 and the location of the imaging device 113 relative to global reference point 201.

At block 511, the location of the target 105 determined at block 510 is used to update the position of LINAC 103 so that the beam of LINAC 103 will intersect target 105. With LINAC 103 properly positioned, the radiation beam is delivered to the target 105 in block 512.

At block 513, if treatment nodes are still pending, then execution proceeds back to block 506, where the treatment process continues. At block 506, the patient is positioned within range of the treatment robot, if necessary. Blocks 506, 507, 508, 509, 510, 511, 512, and 513 are then repeated for subsequent treatment nodes until no more treatment nodes are pending. When no more treatment nodes are pending, the treatment session ends at block 514.

Figure 6:
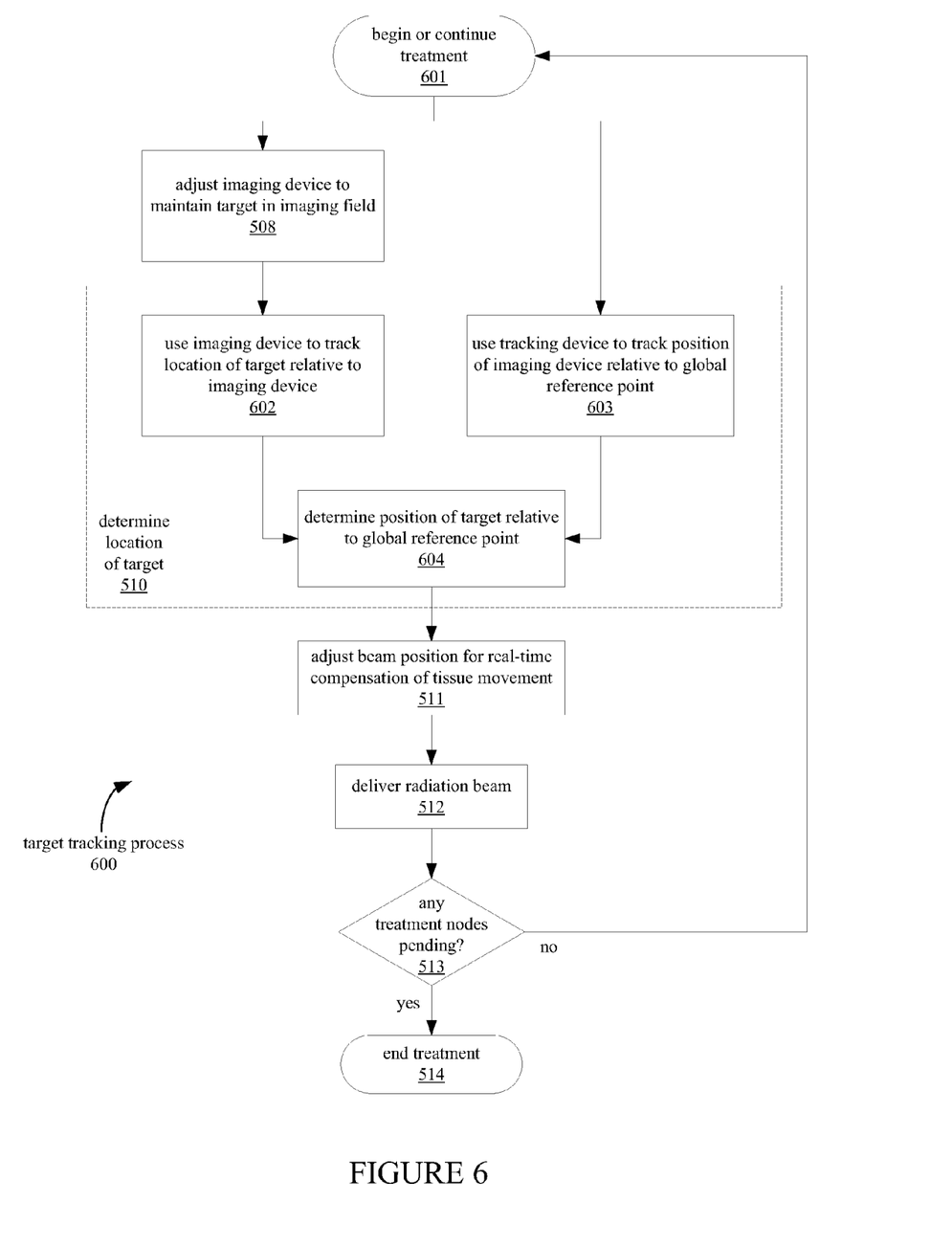
FIG. 6 is a flow diagram illustrating a process for tracking a target, according to one embodiment of the invention.

FIG. 6 is a flow diagram illustrating a process for tracking a target according to one embodiment of the invention. After block 601 of target tracking process 600, the treatment session is in progress. During the treatment session, block 508 provides for adjustment of imaging device 113 to maintain target 105 within imaging field 202 of the imaging device 113. The adjustment is to maintain the quality of the image captured by imaging device 113 so that the image can be used to locate target 105 or so the image can be registered with other images such as CT or X-ray images. The positional adjustment of imaging device 113 may be performed by using a mechanical device such as robotic arm 301 to change the orientation or position of the imaging device 113. In one embodiment, a feedback mechanism may be used, where the robotic arm 301 adjusts the position of imaging device 113 based on an image captured by imaging device 113. For example, if an image captured by imaging device 113 shows that the target 105 is approaching a boundary of imaging field 202, robotic arm may respond by moving imaging device 113 to keep target 105 near the center of imaging field 202. Alternatively, the positional adjustment of imaging device 113 may be performed manually. For example, if ultrasonic imaging system 400 is used as imaging device 113, the ultrasonic transducer 410 may be manually repositioned using slider 413 or attachment point 412. If target 105 is already within imaging field 202, execution of block 508 may not be necessary, and adjustment of imaging device 113 may be avoided.

Block 602 provides for tracking the location of target 105 relative to imaging device 113. The tracking is accomplished by using imaging device 113 to capture an image of target 105. The position and orientation of target 105 within the captured image can then be used to determine the location of target 105 relative to imaging device 113. The result of this determination is target offset 211.

Block 603 may be executed either in parallel or sequentially with blocks 508 and 602. Block 603 provides for determining the position of the imaging device 113 relative to the global reference point 201. Determining the position of the imaging device 113 relative to the global reference point 201 may be accomplished by first using the tracking device 112 to determine an imaging device offset 212 between the tracking device 112 and the imaging device 113, then adding the imaging device offset 212 to a global tracking device offset 213 that indicates an offset between the tracking device 112 and the global reference point 201. For example, if an optical device such as a camera is used as tracking device 112, then tracking device 112 may be used to capture an image that includes imaging device 113. The position and orientation of the imaging device 113 relative to the tracking device 112 can then be determined by reference to the position and orientation of the imaging device 113 as it appears in the captured image. The position of the imaging device 113 relative to the tracking device 112 may be represented as imaging device offset 212. The offset between the imaging device 113 and the global reference point 201 can then be determined by adding the imaging device offset 212 and the global tracking device offset 213. The global tracking device offset 213 may be determined before the beginning of the treatment session.

Alternatively, if the imaging device 113 is mounted on a device such as robotic arm 301, positional sensors on robotic arm 301 may be used to determine the position of imaging device 113 relative to global reference point 201. The position of the imaging device 113 relative to the global reference point 201 may be represented as global imaging device offset 311.

When blocks 602 and 603 have been completed, execution proceeds to block 604, where the position of the target 105 is determined relative to the global reference point 201. The position of target 105 relative to global reference point 201 is the global target offset 210, which may be represented as a three-dimensional vector. The global target offset 210 may be calculated by adding the target offset 211, as determined in block 602, and the offset between imaging device 113 and global reference point 201, as determined in block 603. The resulting global target offset 210 is the offset between the target 105 and the global reference point 201.

In block 511, the global target offset 210 is used to adjust the beam of LINAC 103 so that the beam intersects target 105. In one embodiment, the LINAC 103, which is mounted on robotic arm 102, may be repositioned by robotic arm 102 to maintain an intersection of the LINAC beam with target 105. Alternatively, the treatment couch may be repositioned by robotic arm 106 to maintain an intersection of the LINAC beam with target 105, or a combination of both robotic arms 102 and 106 may be used. Global target offset 210, as determined in block 604, is used to determine how to position LINAC 103 so that the intersection of the LINAC beam with target 105 is maintained.

At block 513, if any treatment nodes are still pending, the treatment is not completed and execution proceeds back to block 601, where the treatment session continues. Blocks 508, 602, 603, 604, 511, 512, and 513 are thus repeated for successive treatment nodes until the treatment has been completed. If no treatment nodes remain pending upon reaching block 513, then the treatment session ends, at block 514.

Alternatively, treatment delivery system 100 may be a type of system other than a robotic arm-based system. For example, treatment delivery system 100 may be a gantry-based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the global reference point to deliver a dose distribution to the target region. In IMRT planning, the optimization algorithm selects subsets of the main beam and determines the amount of time that the patient should be exposed to each subset, so that the prescribed dose constraints are best met. In one particular embodiment, the gantry-based system may have a gimbaled radiation source head assembly.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

Certain embodiments may be implemented as a computer program product that may include instructions stored on a computer-readable medium. These instructions may be used to program a general-purpose or special-purpose processor to perform the described operations. A computer-readable medium includes any mechanism for storing or transmitting information in a form (e.g., software, processing application) readable by a computer. The computer-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

Additionally, some embodiments may be practiced in distributed computing environments where the computer-readable medium is stored on and/or executed by more than one computer system. In addition, the information transferred between computer systems may either be pulled or pushed across the communication medium connecting the computer systems.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   tracking a location of a target using a first imaging device, wherein the target is an anatomical structure in a body and the first imaging device is external to the body;
   determining that the target is not in an imaging field of the first imaging device or is near a boundary of the imaging field;
   automatically adjusting a location of the first imaging device to cause the target to be in the imaging field responsive to determining that the target is not in the imaging field or is near the boundary of the imaging field;
   tracking the location of the first imaging device using a second imaging device, wherein the first imaging device is in a tracking field of the second imaging device while the location of the target is tracked using the first imaging device and while the location of the first imaging device is tracked using the second imaging device; and determining the location of the target relative to a global reference point based on the location of the target from the first imaging device, the location of the first imaging device from the second imaging device, and a location of the second imaging device, wherein determining the location of the target relative to the global reference point comprises determining a first positional offset between the target and the first imaging device, determining a second positional offset between the first imaging device and the second imaging device, determining a third positional offset between the second imaging device and the global reference point, and combining the first positional offset, the second positional offset and the third positional offset.

2. The method of claim 1, wherein the first imaging device is an ultrasound imager.

3. The method of claim 2, wherein the ultrasound imager comprises:
an ultrasonic transducer;
an extension link coupled with the ultrasonic transducer; and
an external unit coupled with the extension link, wherein the ultrasonic transducer is moveable independently from the external unit.

4. The method of claim 1, wherein the second imaging device comprises an optical system.

5. The method of claim 1, wherein the second imaging device is an X-ray imager.

6. The method of claim 1, wherein the first imaging device is mounted on a robotic arm capable of motion with at least five degrees of freedom.

7. The method of claim 6, wherein tracking the location of the first imaging device comprises receiving positional information from the robotic arm.

8. The method of claim 1, wherein the first imaging device is coupled with a treatment couch.

9. The method of claim 8, further comprising applying the first imaging device against a skin surface of a patient using a belt coupled with the first imaging device.

10. The method of claim 1, wherein the location of the target relative to the global reference comprises a global target offset and wherein the method further comprises maintaining an intersection of a beam with the target using the global target offset.

11. The method of claim 10, wherein maintaining the intersection of the beam with the target using the global target offset comprises adjusting at least one of a first robotic arm coupled to a LINAC generating the beam and a second robotic arm coupled to a treatment couch to support a patient having the target.

12. The method of claim 1, wherein the second imaging device is a movable imaging device coupled to a track.

13. An apparatus, comprising:
an automated positioning device;
an imaging device, coupled to the automated positioning device, to track a location of a target relative to the imaging device based on determination of a first positional offset between the target and the imaging device, wherein the target is an anatomical structure in a body and the imaging device is external to the body;
a tracking device to track a location of the imaging device relative to a global reference point based on determination of a second positional offset between the tracking device and the global reference point, wherein the imaging device is to be positioned in a tracking field of the tracking device while the location of the target is tracked by the imaging device and while the location of the imaging device is tracked by the tracking device; and
a processor coupled with the imaging device and the tracking device, wherein the processor is to:
make a determination that the target is not in an imaging field of the imaging device or is near a boundary of the imaging field;
automatically adjust a position of the automated positioning device to cause the target to be in the imaging field of the imaging device responsive to the determination that the target is not in the imaging field or is near the boundary of the imaging field; and
determine the location of the target relative to the global reference point based a combination of the first positional offset and the second positional offset.

14. The apparatus of claim 13, wherein the location of the imaging device is tracked using a tracking device that comprises an optical system.

15. The apparatus of claim 13, wherein the imaging device comprises an ultrasound imager.

16. The apparatus of claim 15, wherein the ultrasound imager comprises:
an ultrasonic transducer;
an extension link coupled with the ultrasonic transducer; and
an external unit coupled with the extension link, wherein the ultrasonic transducer is moveable independently from the external unit.

17. The apparatus of claim 13, wherein the tracking device is an X-ray imager.

18. The apparatus of claim 13, wherein the automated positioning device is a robotic arm capable of movement in at least five degrees of freedom.

19. The apparatus of claim 13, wherein the tracking device tracks the location of the imaging device by determining the position of the automated positioning device.

20. The apparatus of claim 13, wherein the automated positioning device comprises a belt coupled with a treatment couch, wherein the belt is configured to hold the imaging device against a skin surface of a patient.

21. The apparatus of claim 20, wherein the belt comprises a gel container configured to apply gel between the imaging device and the skin surface of the patient.

22. The apparatus of claim 13, wherein the location of the target relative to the global reference comprises a global target offset and wherein the apparatus further comprises a linear accelerator (LINAC) coupled to a robotic arm, wherein the processor is coupled to the robotic arm to adjust a position of the LINAC to maintain intersection of a LINAC beam with the target.

23. The apparatus of claim 13, wherein the location of the target relative to the global reference comprises a global target offset and wherein the apparatus further comprises:
a LINAC to generate a beam; and
a treatment couch coupled to a robotic arm, and wherein the processor is operatively coupled to the robotic arm to adjust a position of the treatment couch to maintain intersection of the LINAC beam with the target.

24. The apparatus of claim 13, wherein the tracking device is a movable tracking device coupled to a track.

25. An apparatus, comprising:
an automated positioning device;
an ultrasonic imager coupled to the automated positioning device, wherein the automated positioning device is to automatically adjust a location of the ultrasonic imager in accordance with a stored imaging device node, and wherein the ultrasonic imager is to track a location of a target, wherein the target is an anatomical structure;

an X-ray imager to track a location of the ultrasonic imager, wherein the ultrasonic imager is to be positioned in a tracking field of the X-ray imager while the location of the target is tracked by the ultrasonic imager and while the location of the ultrasonic imager is tracked by the X-ray imager; and a processor coupled with the ultrasonic imager and the X-ray imager, wherein the processor is to:

determine at least one of a gain setting, a transducer pressure setting, a transmit frequency setting, a receive frequency setting, or a dynamic range setting for the ultrasonic imager based on the stored imaging device node;

adjust at least one of the gain setting, the transducer pressure setting, the transmit frequency setting, the receive frequency setting, or the dynamic range setting; and determine a location of the target relative to a global reference point based on the tracked location of the target using the ultrasound imager and the tracked location of the ultrasonic imager, wherein determining the location of the target relative to the global reference point comprises determining a first positional offset between the target and the ultrasound imager, determining a second positional offset between the ultrasound imager and the x-ray imager, determining a third positional offset between the x-ray imager and the global reference point, and combining the first positional offset, the second positional offset and the third positional offset.

26. The apparatus of claim 25, wherein a transducer of the ultrasonic imager is mounted on a belt coupled with a treatment couch, wherein the belt is configured to hold the ultrasound imager against a skin surface of a patient.

27. The apparatus of claim 25, wherein the location of the target relative to the global reference comprises a global target offset and wherein the apparatus further comprises a linear accelerator (LINAC) coupled to a robotic arm, wherein the processor is coupled to the robotic arm to adjust a position of the LINAC to maintain intersection of a LINAC beam with the target.

28. The apparatus of claim 25, wherein the location of the target relative to the global reference comprises a global target offset and wherein the apparatus further comprises:

a LINAC to generate a beam; and a treatment couch coupled to a robotic arm, and wherein the processor is operatively coupled to the robotic arm to adjust a position of the treatment couch to maintain intersection of the LINAC beam with the target.

* * * * *